US009826907B2

(12) United States Patent
Magi

(10) Patent No.: US 9,826,907 B2
(45) Date of Patent: Nov. 28, 2017

(54) WEARABLE ELECTRONIC DEVICE FOR DETERMINING USER HEALTH STATUS

(71) Applicant: Intel Corporation, Santa Clara, CA (US)

(72) Inventor: Aleksander Magi, Aloha, OR (US)

(73) Assignee: Intel Corporation, Santa Clara, CA (US)

( * ) Notice: Subject to any disclaimer, the term of this patent is extended or adjusted under 35 U.S.C. 154(b) by 6 days.

(21) Appl. No.: 14/142,777

(22) Filed: Dec. 28, 2013

(65) Prior Publication Data

US 2015/0182128 A1    Jul. 2, 2015

(51) Int. Cl.
  G08B 1/08    (2006.01)
  A61B 5/0205  (2006.01)
  A61B 5/145   (2006.01)
  A61B 5/00    (2006.01)
  A61B 5/021   (2006.01)
  A61B 5/024   (2006.01)
  A61B 5/053   (2006.01)

(52) U.S. Cl.
  CPC .......... *A61B 5/0205* (2013.01); *A61B 5/0002* (2013.01); *A61B 5/02055* (2013.01); *A61B 5/14542* (2013.01); *A61B 5/441* (2013.01); *A61B 5/4504* (2013.01); *A61B 5/681* (2013.01); *A61B 5/742* (2013.01); *A61B 5/7445* (2013.01); *A61B 5/0022* (2013.01); *A61B 5/021* (2013.01); *A61B 5/024* (2013.01); *A61B 5/0533* (2013.01); *A61B 5/7475* (2013.01)

(58) Field of Classification Search
  CPC .... A61B 5/681; A61B 5/02438; A61B 5/6824

USPC ................................. 340/539.12; 3/539.12
See application file for complete search history.

(56) References Cited

U.S. PATENT DOCUMENTS

| | | |
|---|---|---|
| 1,656,199 A | 1/1928 | Ensley |
| 5,235,168 A | 8/1993 | Bobba |
| D425,050 S | 5/2000 | Tanigawa |
| D460,373 S | 7/2002 | Cabarbaye |
| D507,550 S | 7/2005 | Kim |
| D522,980 S | 6/2006 | Chu |
| D522,981 S | 6/2006 | Hoehn |
| D533,853 S | 12/2006 | Rashid |

(Continued)

OTHER PUBLICATIONS

U.S. Appl. No. 29/477,898, filed Dec. 28, 2013, and entitled Wearable Computing Device, inventor Aleksander Magi.

(Continued)

*Primary Examiner* — Omeed Alizada
(74) *Attorney, Agent, or Firm* — Patent Capital Group

(57) ABSTRACT

Particular embodiments described herein provide for a wearable electronic device, such as a bracelet, coupled to a plurality of electronic components (which may include any type of components, elements, circuitry, etc.). One particular implementation of a wearable electronic device may include a plurality of sensors configured to measure at least one health parameter of a first user associated with the wearable electronic device, and a control module in communication with the plurality of sensors. The control module includes a processor configured to receive a plurality of health parameter measurements from at least a subset of the plurality of sensors, and determine a general health state of the first user based upon the received health parameter measurements.

16 Claims, 12 Drawing Sheets

(56) References Cited

U.S. PATENT DOCUMENTS

| | | | |
|---|---|---|---|
| D563,339 S | 3/2008 | Tang | |
| D567,113 S | 4/2008 | Tiffoinnet-Airaud | |
| D580,277 S | 11/2008 | Brady et al. | |
| D639,689 S | 6/2011 | Parvex | |
| D651,931 S | 1/2012 | Molik | |
| D710,236 S | 8/2014 | Lee | |
| D719,158 S | 12/2014 | Akana et al. | |
| D729,233 S | 5/2015 | Lee et al. | |
| 2003/0050730 A1* | 3/2003 | Greeven | G06F 19/3406 700/231 |
| 2004/0010185 A1* | 1/2004 | Kimball | A61B 5/14539 600/310 |
| 2005/0021679 A1* | 1/2005 | Lightman et al. | 709/219 |
| 2008/0208009 A1* | 8/2008 | Shklarski | 600/301 |
| 2008/0242943 A1* | 10/2008 | Cuddihy | G06F 19/3418 600/300 |
| 2009/0054737 A1* | 2/2009 | Magar | A61B 5/0205 600/300 |
| 2014/0094675 A1* | 4/2014 | Luna et al. | 600/386 |
| 2015/0052943 A1 | 2/2015 | Inglis | |
| 2015/0164349 A1* | 6/2015 | Gopalakrishnan | A61B 5/02405 600/508 |

OTHER PUBLICATIONS

Restriction Requirement Action in U.S. Appl. No. 29/477,898 dated Jun. 25, 2015.

U.S. Appl. No. 29/477,904, filed Dec. 28, 2013, and entitled Wearable Computing Device, inventor Aleksander Magi.

Restriction Requirement Action in U.S. Appl. No. 29/477,904 dated Jun. 30, 2015.

Uttermost. Avidan Antique Gold Mirror. Aug. 11, 2011 [online], [sited visited Sep. 9, 2015]. Available from Internet, <URL:http://www.uttermost.com/p-2398-avidan.aspx>.

U.S. Notice of Allowance in U.S. Appl. No. 29/477,898 dated Sep. 14, 2015.

U.S. Non Final Action in U.S. Appl. No. 29/477,904 dated Sep. 17, 2015.

U.S. Final Action in U.S. Appl. No. 29/477,904 dated Jan. 15, 2016.

* cited by examiner

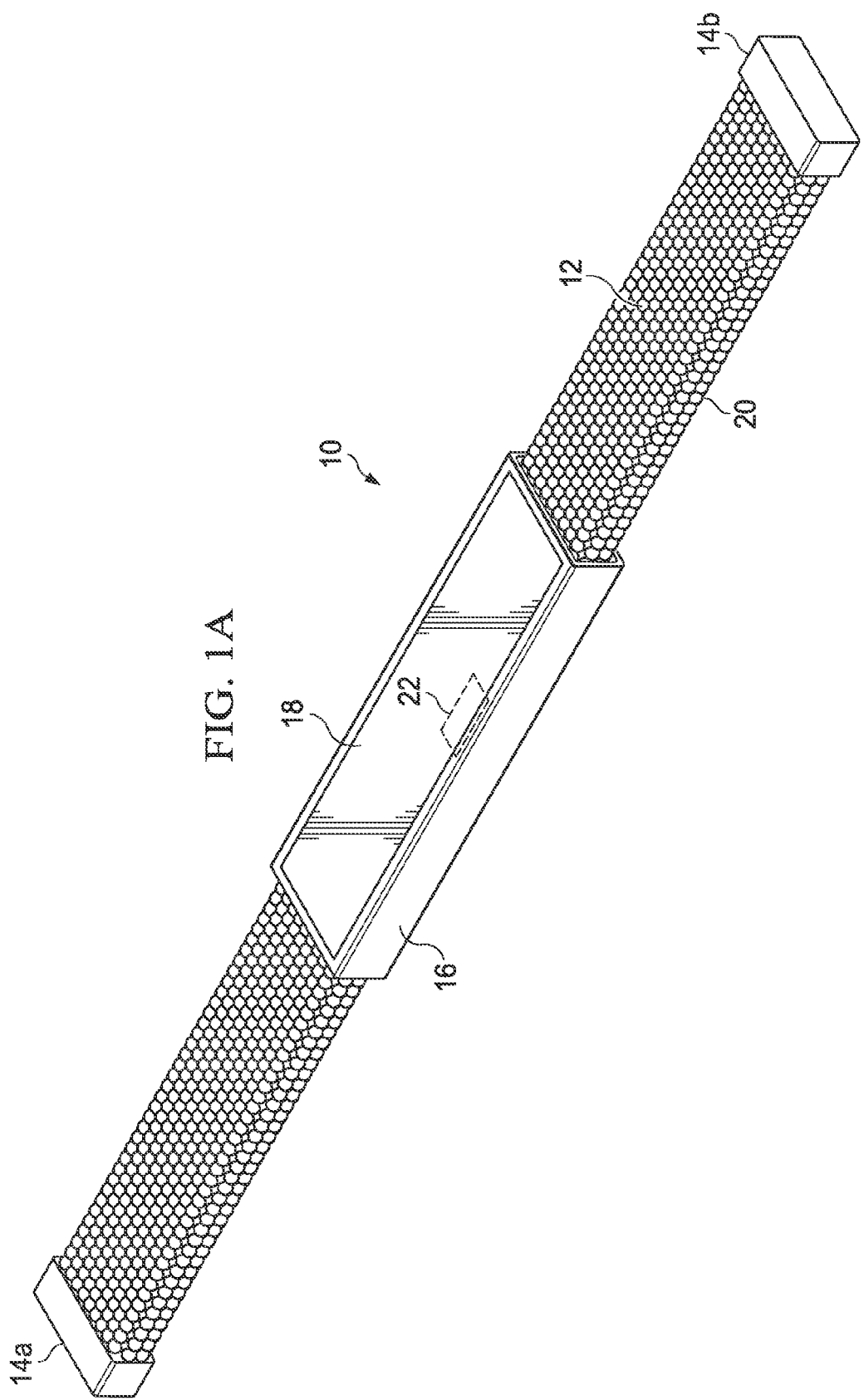

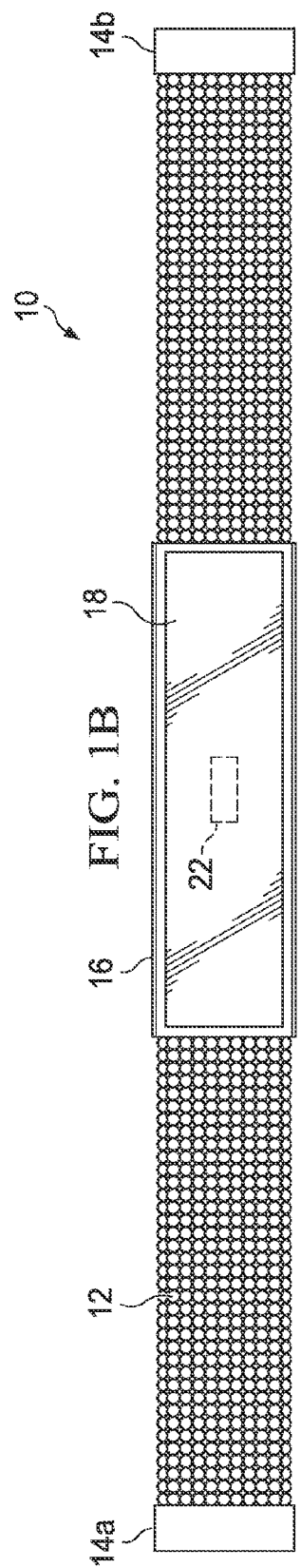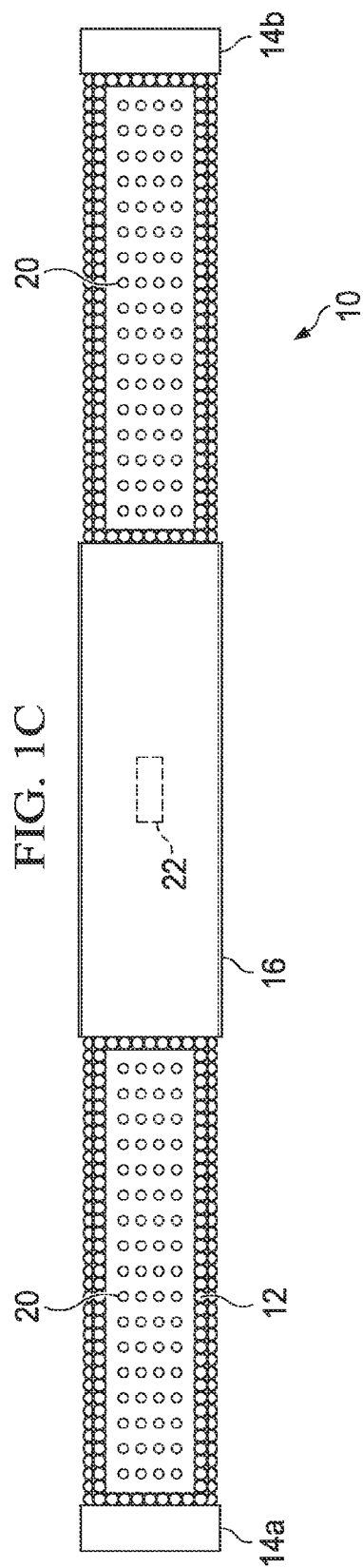

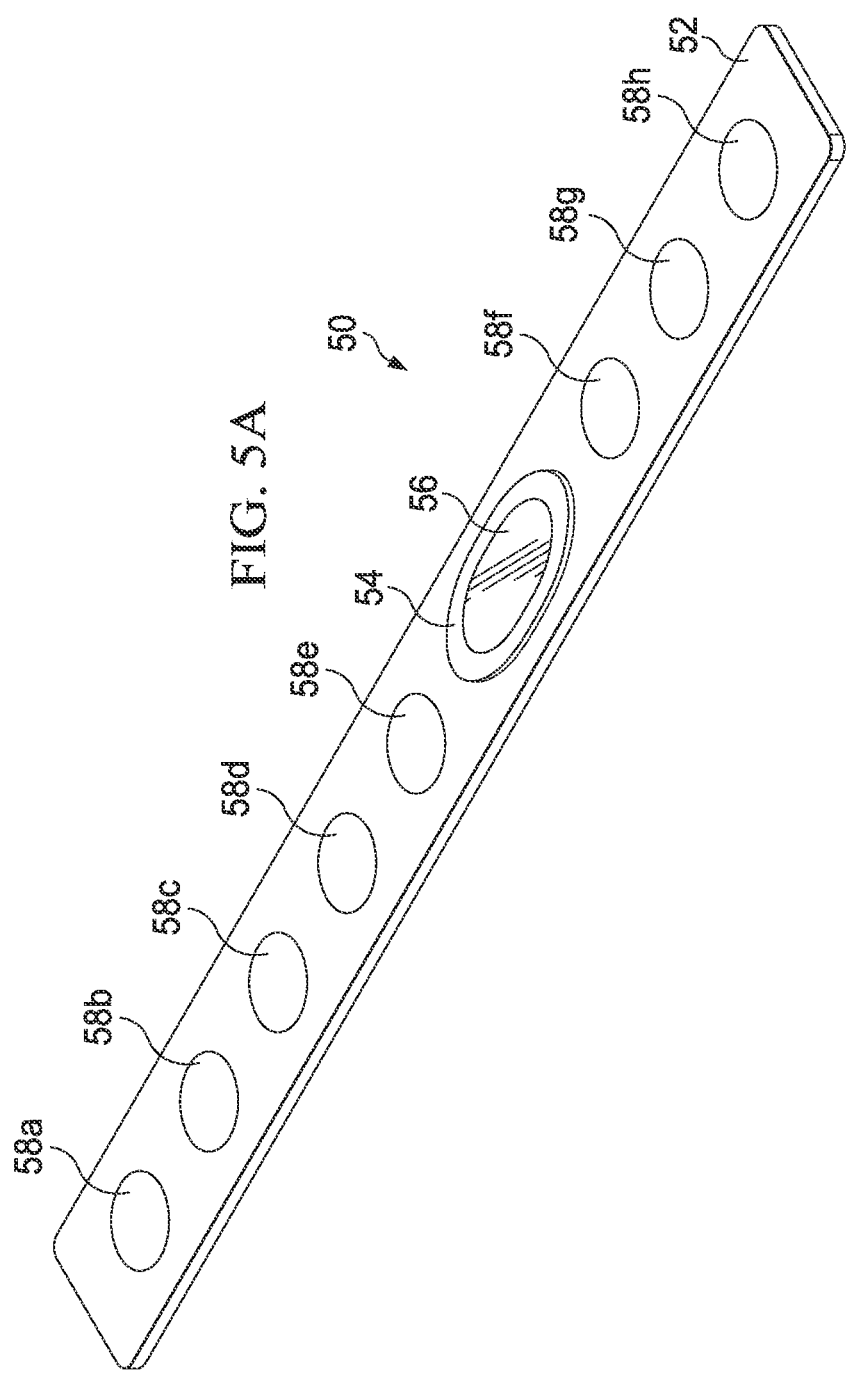

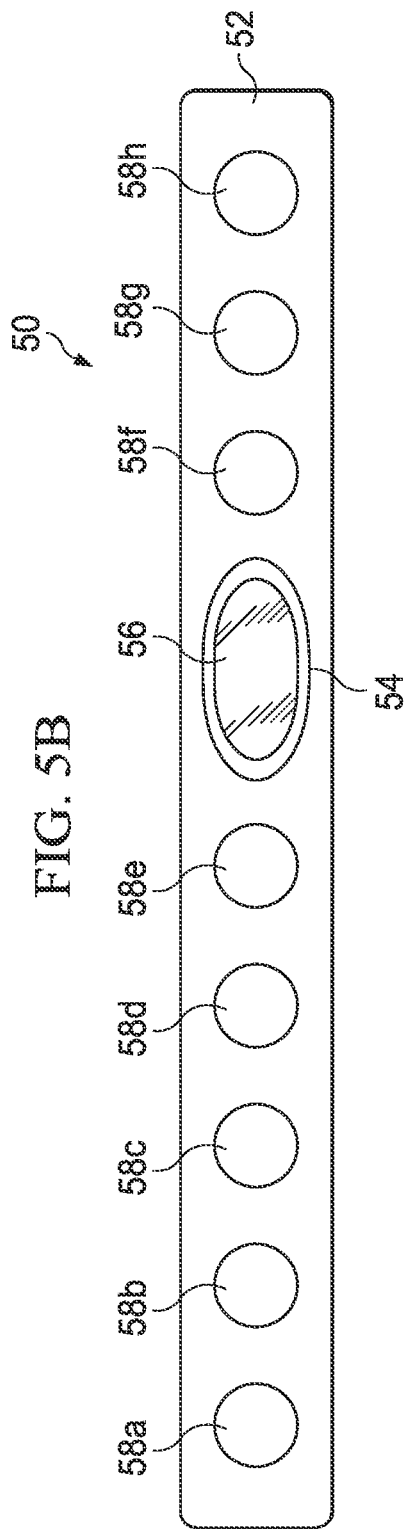
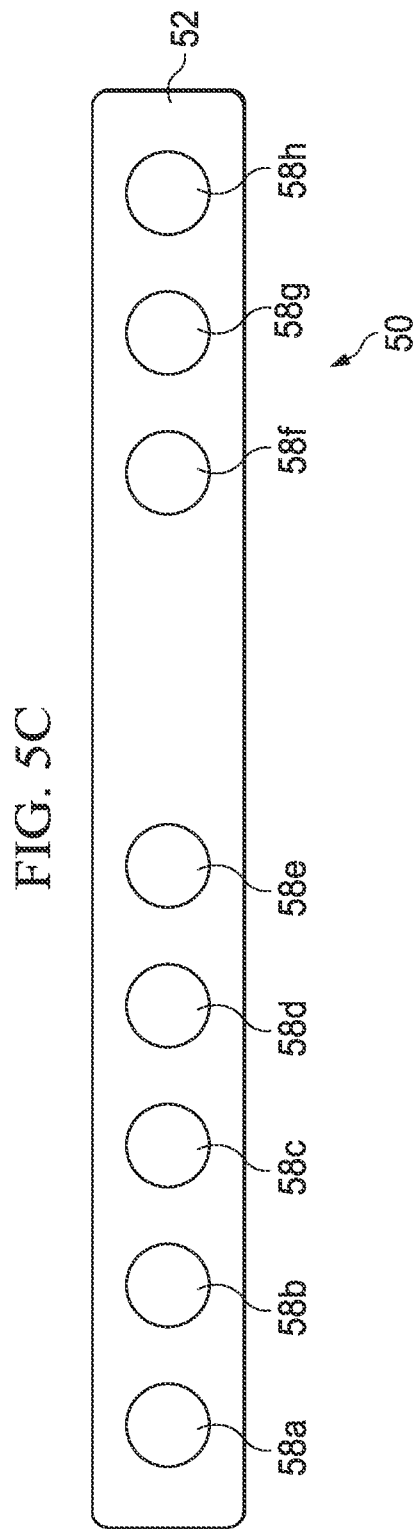

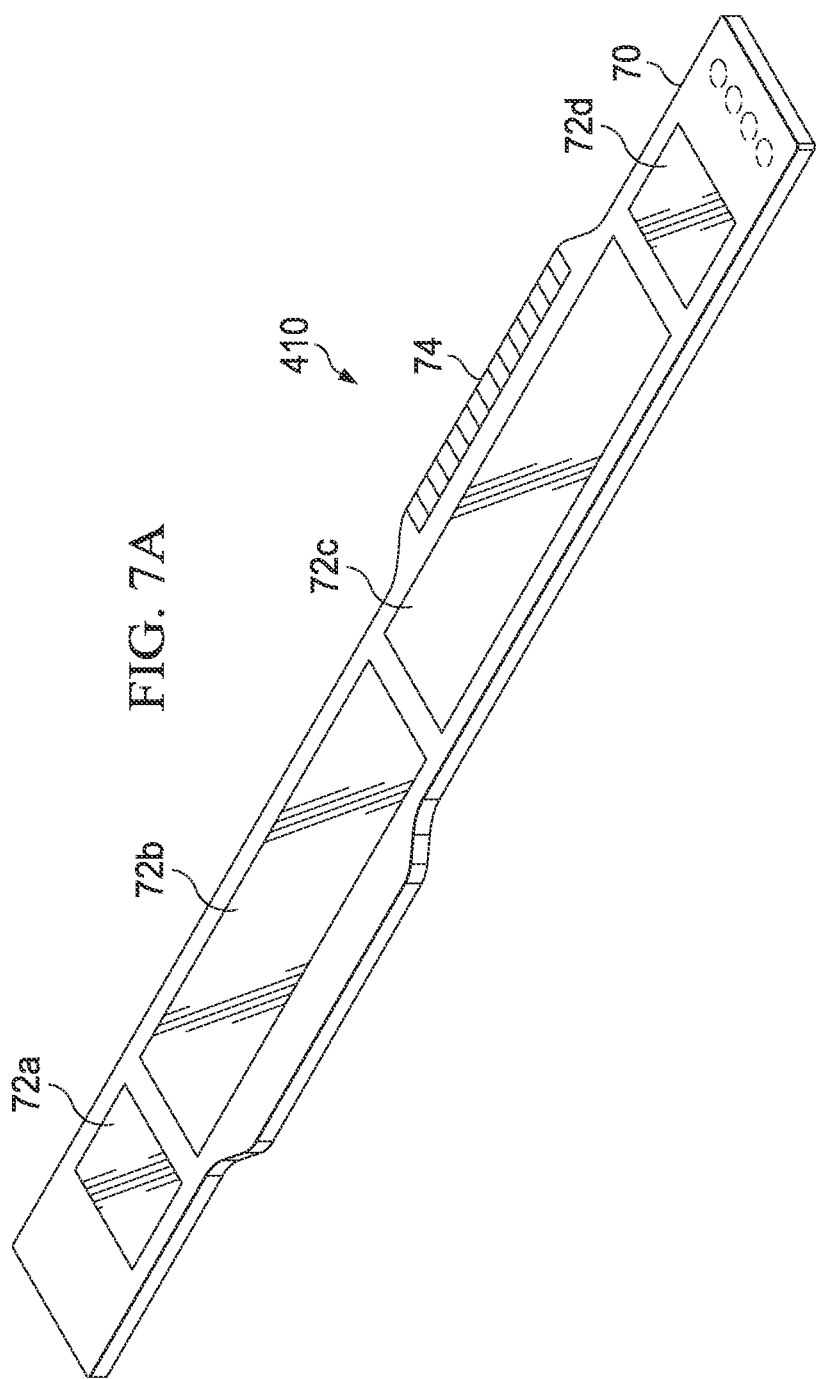

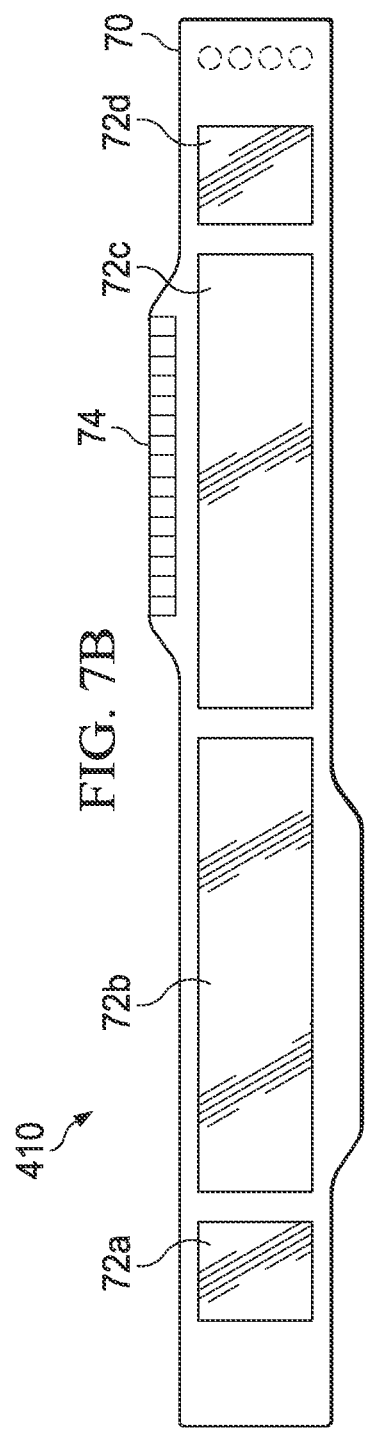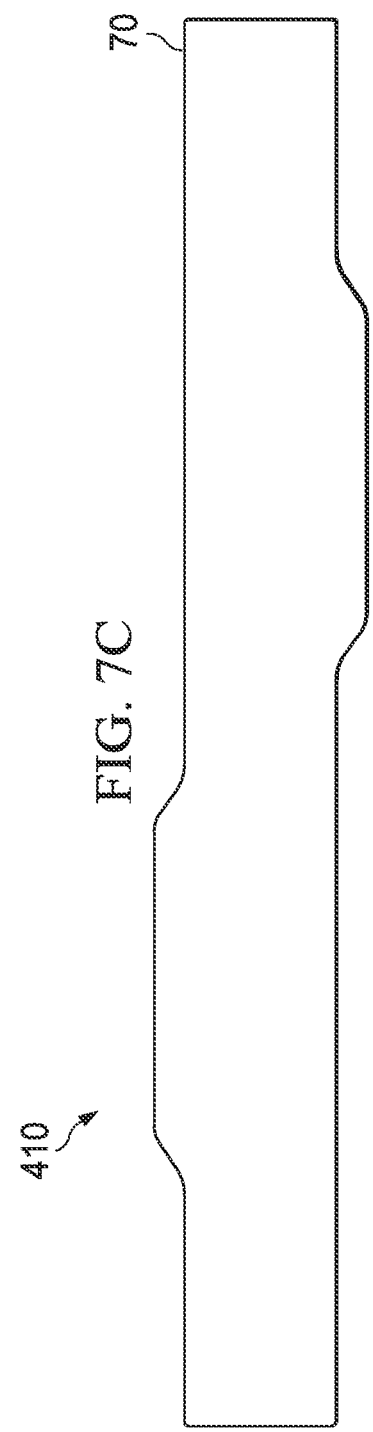

WEARABLE ELECTRONIC DEVICE FOR DETERMINING USER HEALTH STATUS

TECHNICAL FIELD

Embodiments described herein generally relate to a wearable electronic device for determining user health status.

BACKGROUND

End users have more electronic device choices than ever before. A number of prominent technological trends are currently afoot (e.g., mobile electronic devices, smaller electronic devices, increased user connectivity, etc.), and these trends are changing the electronic device landscape. One of the technological trends currently afoot is electronic devices that can be worn by users, sometimes referred to as wearable electronic devices. Wearable electronic devices can be worn on a user's wrist, arm, ankle, etc. Although wearable electronic devices exist that are able to provide body condition information, such as a heart rate of a wearer, these existing device have limited ability to collect accurate data and provide meaningful feedback to the user regarding the user's health condition.

BRIEF DESCRIPTION OF THE DRAWINGS

Embodiments are illustrated by way of example and not by way of limitation in the FIGURES of the accompanying drawings, in which like references indicate similar elements and in which:

FIGS. 1A-1C are simplified views illustrating a wearable electronic device for determining user health status in accordance with one embodiment of the present disclosure;

FIGS. 5A-5C are simplified views illustrating a wearable electronic device for determining user health status in accordance with another embodiment of the present disclosure;

FIGS. 7A-7C are simplified views illustrating a monitoring device for receiving user health status from a wearable electronic device in accordance with an embodiment of the present disclosure;

Figure 2:
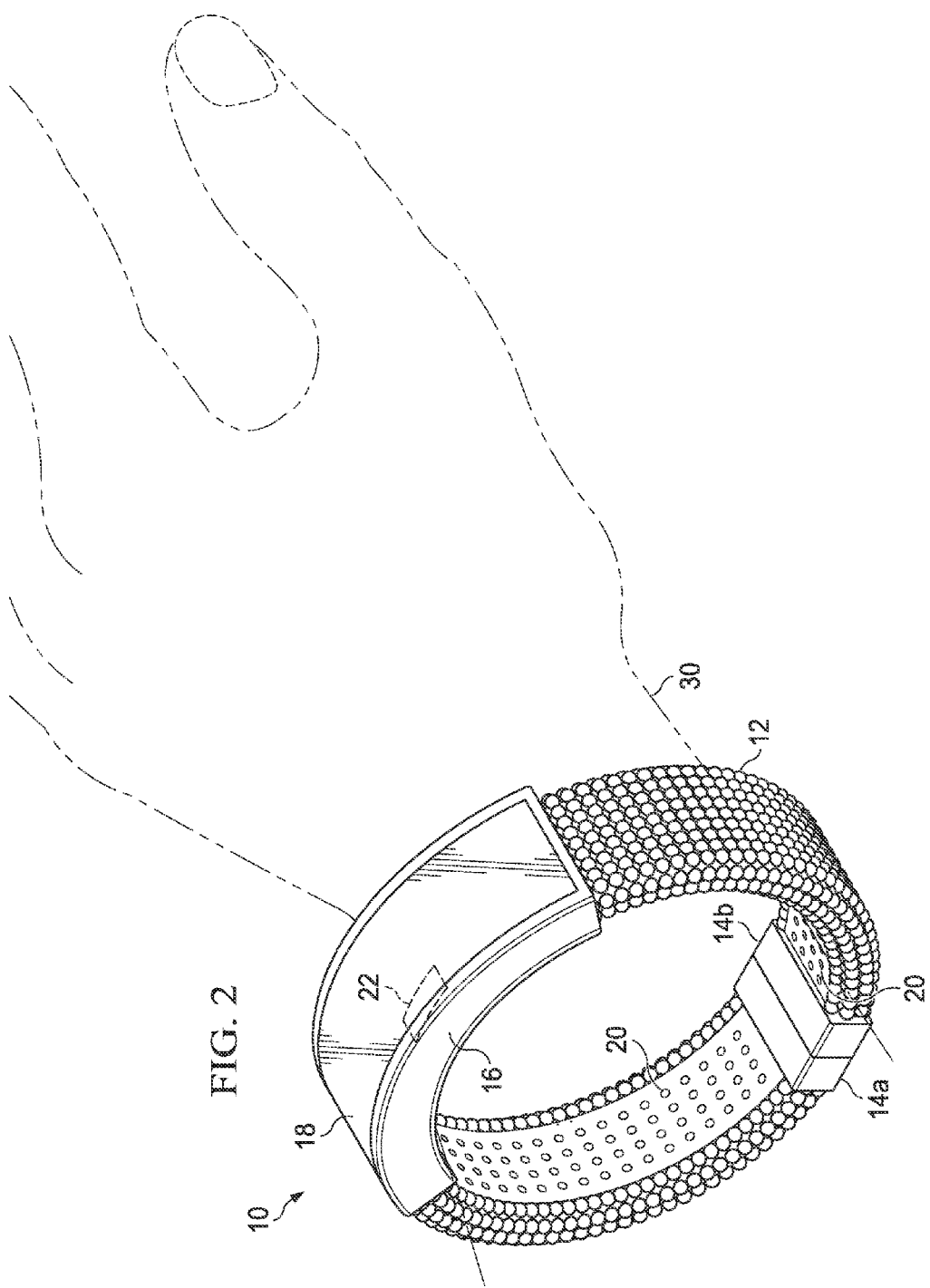
FIG. 2 illustrates an embodiment of an example procedure for determining user health status using a wearable electronic device.

The FIGURES of the drawings are not necessarily drawn to scale, as their dimensions can be varied considerably without departing from the scope of the present disclosure.

DETAILED DESCRIPTION OF EXAMPLE EMBODIMENTS

Overview

Example embodiments described herein provide for a wearable electronic device, such as an electronic bracelet, that includes a circuit board coupled to a plurality of electronic components (which may include any type of components, elements, circuitry, etc.). One particular implementation of a wearable electronic device may include a plurality of sensors configured to measure at least one health parameter of a first user associated with the wearable electronic device, and a control module in communication with the plurality of sensors. The control module includes a processor configured to receive a plurality of health parameter measurements from at least a subset of the plurality of sensors, and determine a general health state of the first user based upon the received health parameter measurements.

In at least one embodiment, the wearable electronic device further includes a display configured to provide feedback indicative of the determined general health state to the first user. In still another embodiment, the processor is further configured to send a first message including information indicative of the general health state to an electronic device associated with a second user. In still another embodiment, the processor is further configured to receive a second message from the electronic device associated with the second user, wherein the second message includes a request for additional information from the first user. In another embodiment, the processor is further configured to send a third message to the electronic device associated with the second user, wherein the third message includes the requested additional information from the first user.

In another embodiment, the electronic device associated with the second user includes another wearable electronic device. In another embodiment, the processor is further configured to determine the general health state of the first user by determining an overall value for one or more particular health parameter measurements, and determining whether the overall value of each health parameter measurement is at an acceptable level. In another embodiment, the processor is further configured to provide feedback to the first user indicating that the first user has achieved an optimal health state if each of the overall health parameter measurements are determined to be at an acceptable level. In another embodiment, the wearable electronic device further includes a strap portion, wherein the plurality of sensors are disposed upon a portion of a surface of the strap portion. In still another embodiment, the plurality of health measurements are associated with one or more health parameters of the user, wherein each health parameter is configured to be measured at a plurality of locations upon the surface of the strap portion.

In another embodiment, the plurality of sensors comprise a sensor array. In still another embodiment, at least one of the plurality of sensors includes at least one of a skin sensor, a temperature sensor, a pulse sensor and a galvanic skin response sensor. In still another embodiment, the at least one health parameter includes one or more of body temperature, air temperature, pulse, galvanic skin response, skin health, bone health, blood health, heart rate, oxygen level, and blood pressure.

Another particular implementation of a wearable electronic device may include a plurality of sensors configured to measure at least one health parameter of a first user associated with the wearable electronic device, and a control module in communication with the plurality of sensors with the control module including logic, at least a portion of which is partially implemented in hardware. The logic may be configured to receive a plurality of health parameter measurements from at least a subset of the plurality of sensors, and determine a general health state of the first user based upon the received health parameter measurements.

Another particular implementation includes a method including receiving a plurality of health parameter measurements from a subset of a plurality of sensors of a wearable electronic device, wherein each of the plurality of sensors is configured to measure at least one health parameter of a first user associated with the wearable electronic device. The method further includes determining, by the wearable electronic device, a general health state of the first user based upon the received health parameter measurements.

Example Embodiments

The following detailed description sets forth example embodiments of apparatuses, methods, and systems relating to configurations for a wearable electronic device for measuring. Features such as structure(s), function(s), and/or characteristic(s), for example, are described with reference to one embodiment as a matter of convenience; various embodiments may be implemented with any suitable one or more of the described features.

FIG. 1A is a simplified orthographic view illustrating a wearable electronic device 10 for determining user health status in accordance with one embodiment of the present disclosure. Wearable electronic device 10 can include a strap portion 12 having a first clasp portion 14a and a second clasp portion 14b at opposing ends of strap portion 12. In at least one embodiment, first clasp portion 14a and second clasp portion 14b are configured coupled together to allow wearable electronic device 10 to be worn around a wrist of a user. In the embodiment illustrated in FIG. 1A, wearable electronic device 10 further includes a housing portion 16 including a display screen 18 disposed on an upper surface of a housing thereof. Strap portion 12 includes a sensor array 20 disposed upon a bottom surface thereof. Sensor array 20 includes a plurality of skin sensors configured to measure one or more health parameters of a user via contact or proximity of to a skin surface of the user while being worn. In accordance with various embodiments, housing portion 16 includes a control module 22 having components, circuitry, and/or logic configured to receive the measured one or more health parameters, determine a general health state of the user based upon the received health parameters, and provide feedback indicative of the determined general health state to the user via display screen 18. In one or more embodiments, one or more of strap portion 12, housing portion 16, and display screen 18 may be composed of a flexible material to allowing bending to facilitate wearing of wearable electronic device 10 around the wrist or other body portion of the user.

In one or more embodiments, strap portion 12 may be of a solid unibody construction having a decorative beaded pattern thereon (as shown in FIGS. 1A-1C) or may include links, chains, cables, weaves, combinations thereof or the like. In some embodiments, wearable electronic device 10 can include a strap that is formed as a solid strap without a latch portion. The ornamental design and material construction of strap portion 12 can be adjusted in any manner to suit any designer, manufacturer and/or vendor without departing from the scope of the embodiments described in the present disclosure.

In one or more embodiments, display screen 18 is a screen that can be a liquid crystal display (LCD) screen, transparent LCD screen, light-emitting diode (LED) display screen, transparent LED display screen, organic light-emitting diode (OLED) display screen, transparent LED display screen or any other suitable display screen system. Display screen 18 may also be a touchscreen display, which may include a capacitive or resistive touchscreen layer over the screen of display screen 18.

FIG. 1B is a simplified top plan view of wearable electronic device 10 in which display screen 18 is shown disposed on the top surface of housing portion 16 so that it may be visible when wearable electronic device 10 is being worn by the user. FIG. 1C illustrates a simplified bottom view of wearable electronic device 10 in which the sensor array 20 is shown on a bottom surface of strap portion 12 so that it may be in contact with a portion of the skin of the user when wearable electronic device 10 is being worn by the user.

In one or more embodiments, wearable electronic device 10 may further include a wireless communication module configured to communicate the determined general health state of the user with other wireless electronic devices such as a wireless communication device associated with the user or an electronic communication device associated with another user. In a particular embodiment, the wireless communication module may be located within housing portion 16. In at least one embodiment, connecting of first clasp portion 14a to second clasp portion 14b may initiate powering up of wearable electronic device 10. In still other embodiments, strap portion 12 may be constructed as a generally ring shaped form with an open portion between ends to facilitate placing of wearable electronic device 10a upon a wrist of a user.

FIG. 2 illustrates an embodiment of an example procedure for determining user health status using wearable electronic device 10. In the embodiment illustrated in FIG. 2, wearable electronic device 10 is worn upon a wrist 30 of a user. The user may initiate a measurement procedure via a touch input upon a graphical user interface (GUI) provided by display screen 18. In response to the touch input, control module 22 within housing portion 16 determines a subset of the sensors of sensor array 20 to be utilized to measure one or more health parameters and/or biometric parameters, and receives a plurality of health parameter measurements from the determined subset sensors of sensor array 20. For example, health parameters measured by one or more sensors of sensor array 20 may include one or more of temperature, pulse, galvanic skin response, skin health, bone health, blood health, heart rate, oxygen levels, blood pressure or any other suitable health parameters. In a particular embodiment, the sensors of sensory array 20 may include one or more of temperature sensors for body temperature and/or air temperature, pulse sensors to measure pulse rate, and/or galvanic skin response sensors for measuring, for example, stress. In a particular embodiment, the subset of the sensors includes all of the sensors of sensor array 20.

In accordance with various embodiments, sensor array 20 may be used to improve the accuracy of a determined health parameter. For example, the control module 22 may calculate an average value or mean value of the received measurements for a particular health parameter, such as heart rate, to determine an overall value for the particular health parameter. In a particular embodiment, the sensor array 20 may be arranged substantially around the entire bottom surface of strap portion 12 to allow substantially three hundred and sixty (360) degrees of measurement of health parameters around wrist 30. In one or more embodiments, sensory array 20 may include a repeated grid of sensors. In one or more embodiments, sensor array 20 may include different types of sensors that may be arranged in a cluster, for example in a row or in a circle, around a single position on strap portion 12 in which the cluster of sensors is considered as one sensor group. Because strap portion 12 may move or slide around the wrist 30 of the user during use and no single sensor can provide an accurate measurement all of the time during such movement, an array of sensor groups may be arranged to span the length of strap portion 12 to optimize the quality of the health parameter readings. In a particular embodiment, each sensor in each group may measure a particular health parameter and control module 22 may included logic configured to coalesce the health parameter measurements into more accurate data to provide more accurate data than a single group of sensors may provide. In a particular embodiment, a plurality of health measurements are associated with one or more health parameters of the user and each health parameter is configured to be measured at a plurality of locations upon the surface of strap portion 12 to provide redundancy and increase the accuracy of measurement of each health parameter.

Control module 22 may be further configured to determine a general health state for the user based using one or more algorithms based upon a combination of the received health parameters, and store the general health state in a memory. An example general health state algorithm may include determining whether each overall value of each health parameter measurement is at an acceptable level. If each of the overall health parameter measurements are determined to be at an acceptable level, control module 22 may cause display screen 22 to indicate to the user that the user has achieved an optimal "Prime" health state. Alternately, if the general health state of the user is determined to be poor, the user may be provided with an indication of relative "poor" health.

In one or more embodiments, wearable electronic device 10 may include one or more power management functions such as powering down to a lower power state after a measurement reading has been taken, periodically determining a location of wearable electronic device 10, and powering back up if movement has occurred. In one or more embodiments, information indicative of the general health state of the user may be sent to another device either in a surrounding area or to a remote device over a network. In a particular embodiment, the information indicative of the general health state of the user may be sent to a second device configured to store the information in a database and alert and/or notify a second user of the second device of the general health state of the user of wearable electronic device 10. The second user may include, in some examples, a nurse or doctor at a hospital, or a coach/trainer at an athletic event.

Figure 3:
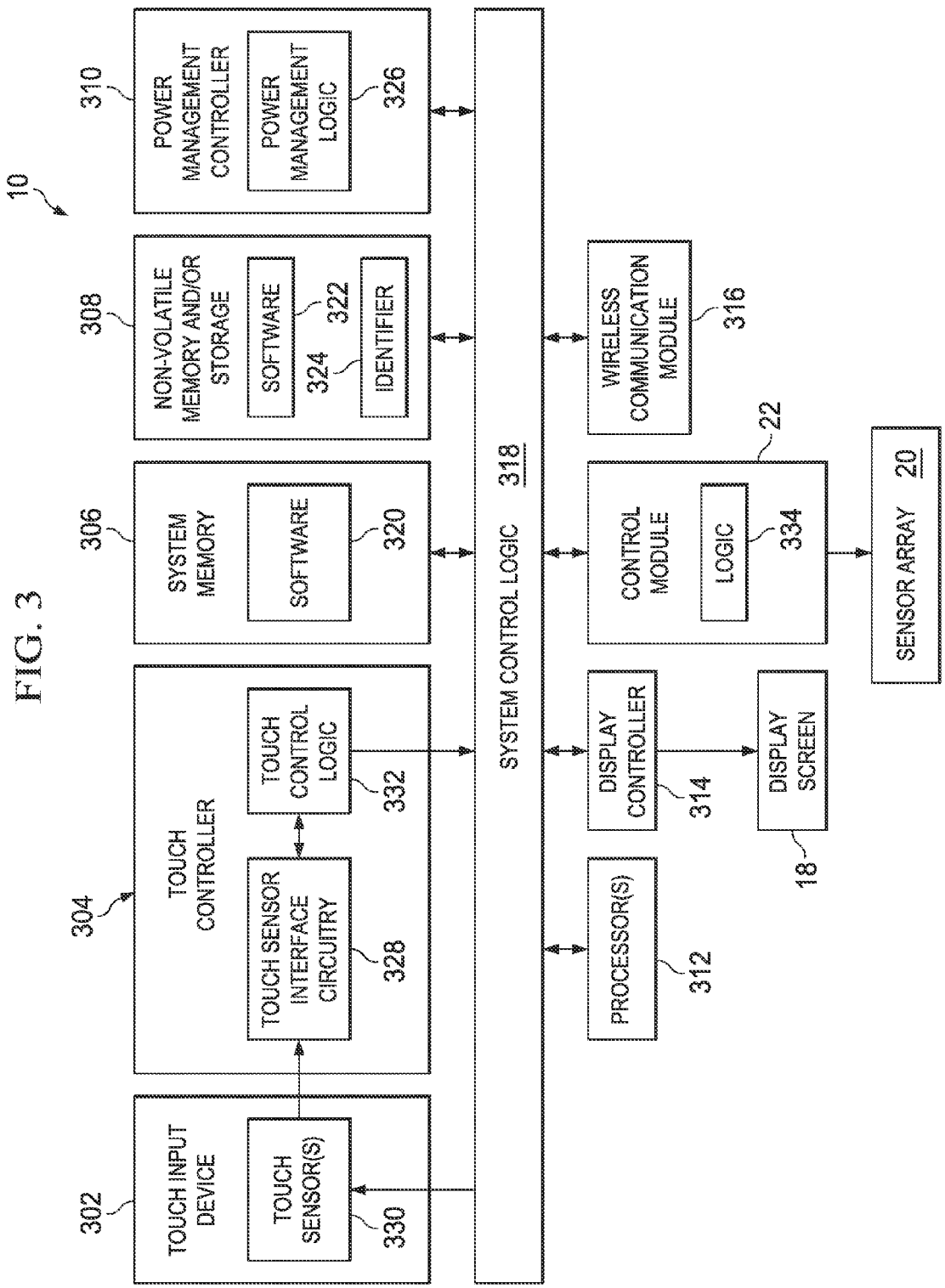
FIG. 3 is a simplified block diagram illustrating example logic that may be used to execute activities associated with wearable electronic device in accordance with one embodiment.

FIG. 3 is a simplified block diagram illustrating example logic that may be used to execute activities associated with wearable electronic device 10 in accordance with one embodiment. In at least one example embodiment, wearable electronic device 10 can include a touch input device 302, a touch controller 304, a system memory 306, a non-volatile memory and/or storage 308, a power management controller 310, processor(s) 312, display controller 314, control module 22, and wireless communication module 316, each of which is coupled to system control logic 318. Display controller 314 is in further communication with display screen 18, and control module 22 is in further communication with sensory array 20. In one or more embodiments, touch input device 302, touch controller 304, system memory 306, non-volatile memory and/or storage 308, power management controller 310, processor(s) 312, display controller 314, control module 22, wireless communication module 316, system control logic 318, and display screen 18 may be disposed at least partially within or upon a surface of housing 16.

Hence, the basic building blocks of any wearable electronic device system (e.g., processor, controller, memory, I/O, display, etc.) can be used in conjunction with the teachings of the present disclosure. Certain components could be discrete or integrated into a System on Chip (SoC). In alternate implementations, instead of wearable electronic devices, certain alternate embodiments deal with mobile phones, tablet devices, etc.

System control logic 318, in at least one embodiment, can include any suitable interface controllers to provide for any suitable interface to at least one processor 312 and/or to any suitable device or component in communication with system control logic 318. System control logic 318, in at least one embodiment, can include one or more memory controllers to provide an interface to system memory 306. System memory 306 may be used to load and store data and/or instructions, for example, for wearable electronic device 10. System memory 306, in at least one embodiment, can include any suitable volatile memory, such as suitable dynamic random access memory (DRAM) for example. System memory 306 may store suitable software 320 and/or non-volatile memory and/or storage device(s).

Non-volatile memory and/or storage device(s) 308 may be used to store data and/or instructions, for example within software 322. Non-volatile memory and/or storage device(s) 308 may include any suitable non-volatile memory, such as flash memory for example, and/or may include any suitable non-volatile storage device(s), such as one or more hard disc drives (HDDs), solid state drives (SSDs), etc. for example. In various embodiments, non-volatile memory and/or storage 308 includes a device identifier 324 associated with wearable electronic device 10 to uniquely identify wearable electronic device 10 from among other devices that may be associated with other users.

Power management controller 310 may include power management logic 326 configured to control various power management and/or power saving functions. In at least one example embodiment, power management controller 310 is configured to reduce the power consumption of components or devices of wearable electronic device 10 that may either be operated at reduced power or turned off when the wearable electronic device is in an inactive state (e.g., not being accessed, etc.). For example, in at least one embodiment, when charm device wearable electronic device 10 is in an inactive state, power management controller 310 may perform one or more of the following: power down the unused portion of touch input device 302; allow one or more of processor(s) 312 to go to a lower power state if less computing power is required during times of inactivity; power down display screen 18, and shutdown any devices and/or components that may be unused when wearable electronic device 10 is in an inactive state. System control logic 318, in at least one embodiment, can include one or more I/O controllers to provide an interface to any suitable input/output device(s).

For at least one embodiment, at least one processor 312 may be packaged together with logic for one or more controllers of system control logic 318. In at least one embodiment, at least one processor 312 may be packaged together with logic for one or more controllers of system control logic 318 to form a System in Package (SiP). In at least one embodiment, at least one processor 312 may be integrated on the same die with logic for one or more controllers of system control logic 318. For at least one embodiment, at least one processor 312 may be integrated on the same die with logic for one or more controllers of system control logic 318 to form a System on Chip (SoC).

For touch input, touch controller 304 may include touch sensor interface circuitry 328 coupled to one or more touch sensor(s) 330 to detect touch input(s) from the user upon display screen 18. Touch sensor interface circuitry 328 may include any suitable circuitry that may depend, for example, at least in part on the touch-sensitive technology used for touch input device 302.

Further for touch control, touch control logic 332 may be coupled to touch sensor interface circuitry 328 to help control touch sensor interface circuitry 328 in any suitable manner to detect touch input from the user. For touch control, touch control logic 332 for at least one example embodiment may also be coupled to system control logic 318 to output in any suitable manner digital touch input data corresponding to one or more touch inputs detected by touch sensor interface circuitry 328. Touch control logic 332 may be implemented using any suitable logic, including any suitable hardware, firmware, and/or software logic (e.g., non-transitory tangible media), that may depend, for example, at least in part on the circuitry used for touch sensor interface circuitry 328.

For touch control, touch control logic 332 may be coupled to system control logic 318 to output digital touch input data to system control logic 318 and/or at least one processor 312 for processing. At least one processor 312 for at least one embodiment may execute any suitable software to process digital touch input data output from touch control logic 332. Suitable software may include, for example, any suitable driver software and/or any suitable application software. Display controller 314 is configured to control the display functions of display screen 18.

Control module 22 includes logic 334 configured to receive health parameter measurements from sensor array 20 and to perform the various health status determination functions as described herein. In one or more embodiments, wearable electronic device 10 can include wireless communication module 316 (e.g., Wi-Fi module, Bluetooth™ module, near field communication (NFC) module, or other wireless communication circuitry) to allow wearable electronic device 10 to communicate with one or more other electronic devices (wearable or not wearable) on a network through a wireless connection. The wireless connection may be any 3G/4G/LTE cellular wireless connection, WiFi/WiMAX connection, Bluetooth™ connection, or some other similar wireless connection. In one or more embodiments, the wireless communication circuitry can be configured to provide for two-way radio communications with another two-way radio capable device. In an embodiment, a plurality of antennas can be provisioned in conjunction with charm device 16a, which may be associated with wireless connection activities. The antennas are reflective of electrical components that can convert electric currents into radio waves or radio signals. Wearable electronic device 10 may include logic to determine a best mode of communication using various signal measurement techniques, including, but not limited to, wireless beacons (to locate one or more Wi-Fi networks), received signal strength indicator (RSSI), link quality indicator (LQI), measurement reports for one or more 3G/4G/LTE cellular wireless connections, combinations thereof or the like.

In one or more embodiments, wearable electronic device 10 may be configured to operate using a replaceable battery, or in some cases, may be configured to operate using a rechargeable battery, each of which may be housed in housing portion 16. In some embodiments, charm device 16a may include charging contacts configured on the outer surface of housing portion 16, which can be used in combination with a charging device to facilitate charging a rechargeable battery within wearable electronic device 10. Virtually any means may be used to provide power and/or charging for wearable electronic device 10, and, thus, are clearly within the scope of the present disclosure.

Figure 4:
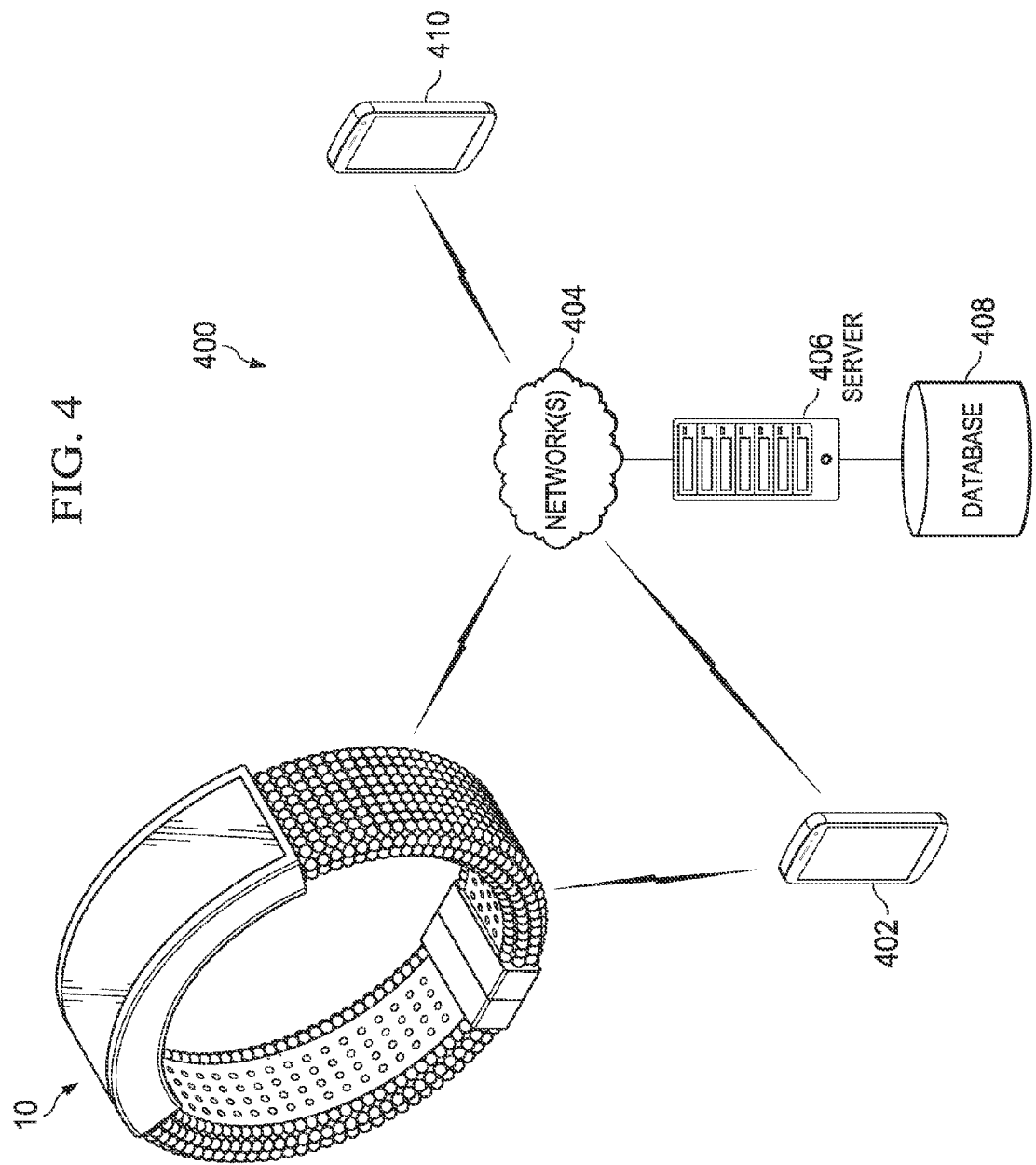
FIG. 4 is a simplified block diagram illustrating an embodiment of a communication system for wireless communication between a wearable electronic device and a monitoring device.

Referring now to FIG. 4, FIG. 4 is a simplified block diagram illustrating an embodiment of a communication system 400 for wireless communication between wearable electronic device 10 and a monitoring device. Communication system 400 includes wearable electronic device 10, a first electronic communication device 402, one or more networks 404, a server 406, a database 408, and a monitoring device 410. In at least one embodiment, wearable electronic device 10 is in communication with first electronic communication device 402 via a first wireless connection. In at least one embodiment, first electronic communication device 402 is in communication with network(s) 404 via a second wireless connection. In particular embodiments, one or more of the first wireless connection and second wireless connection may be any 3G/4G/LTE cellular wireless, WiFi/WiMAX connection, Bluetooth™ or some other similar wireless connection.

Network(s) 404 may be a series of points or nodes of interconnected communication paths for receiving and transmitting packets of information that propagate through network(s) 404. Network(s) 404 offers a communicative interface and may include any local area network (LAN), wireless local area network (WLAN), metropolitan area network (MAN), Intranet, Extranet, WAN, virtual private network (VPN), cellular network or any other appropriate architecture or system that facilitates communications in a network environment. Network(s) 404 can comprise any number of hardware or software elements coupled to (and in communication with) each other through a communications medium. First electronic communication device 402 and/or monitoring device 410 may be a computer (e.g., notebook computer, laptop, tablet computer or device), a phablet, a cellphone, a personal digital assistant (PDA), a smartphone, a movie player of any type, router, access point, another wearable electronic device or other device that includes a circuit board coupled to a plurality of electronic components (which includes any type of components, elements, circuitry, etc.). In one or more embodiments, monitoring device 410 includes a portable and/or wearable electronic device. In one or more embodiments, wearable electronic device 10 and first electronic communication device 402 are associated with a first user, and monitoring device 410 is associated with a second user.

Server 406 is in communication with network(s) 404 and in further communication with database 408. In one or more embodiments, server 406 is configured to receive one or more messages transmitted by wearable electronic device 10 indicative of the general health state of the user associated with wearable electronic device 10 and store the information indicative of the general health state of the user in association with a device identifier associated with wearable electronic device 10. In alternative embodiments, the general health state of the user may be stored in associated with a user identifier associated with the user of wearable electronic device 10. Server 406 may be further configured to send a message including the information indicative of the general health state of the user associated with wearable electronic device 10 to monitoring device 410. A second user associated with monitoring device 410 may then view the general health information associated with the first user in a display of monitoring device 410.

In example operations associated with FIG. 4, wearable electronic device 10 may measure health parameters of a first user wearing wearable electronic device 10 and determine a general health state of the first user. Wearable electronic device 10 may then send a first message indicative of the general health state of the first user to server 406. In one embodiment, wearable electronic device 10 may send the first message to server 406 via direct communication with network(s) 404. In still another embodiment, wearable electronic device 10 may send the first message to first electronic device 10, and first electronic device 10 may send the first message to server 406 via network(s) 404. Server 406 may then send a second message including information indicative of the general health state of the first user to monitoring device 410 associated with the second user via network(s) 404. The display of monitoring device 10 may then notify the second user by presenting an indication of the general health state of the first user to the second user.

In accordance with some embodiments, the second user may utilize monitoring device 10 to send a follow-up request message to first user for additional information regarding the health condition of the first user. For example, the second user may send the request message including an inquiry of "How are you doing?". The first user may then utilize wearable electronic device 10 to send a response message including a response to the inquiry to monitoring device 410. For example, the first user may send a response message including a response of "I am OK" to the second user.

FIG. 5A is a simplified orthographic view illustrating a wearable electronic device 50 for determining user health status in accordance with another embodiment of the present disclosure. Wearable electronic device 50 can include a strap portion 52 to allow wearable electronic device 10 to be worn around a wrist of a user. In the embodiment illustrated in FIG. 5A, wearable electronic device 10 further includes a housing portion 54 including a display screen 56 disposed on an upper surface of a housing thereof. Strap portion 52 includes a sensor array include a plurality of skin sensors 58a-58h disposed therein. Skin sensors 58a-58h are configured to include an lower sensor surface functioning configured to measure one or more health parameters of a user via contact or proximity of to a skin surface of the user while being worn. In some embodiments, an upper surface of skin sensors 58a-58h may serve a decorative function for wearable electronic device 50. In accordance with various embodiments, housing portion 54 includes a control module in communication with skin sensors 58a-58h and having components, circuitry, and/or logic configured to receive the measured one or more health parameters, determine a general health state of the user based upon the received health parameters, and provide feedback indicative of the determined general health state to the user via display screen 56. In one or more embodiments, one or more of strap portion 52, housing portion 54, and display screen 56 may be composed of a flexible material to allowing bending to facilitate wearing of wearable electronic device 50 around the wrist or other body portion of the user.

In one or more embodiments, strap portion 52 may be of a solid unibody construction or may include links, chains, cables, weaves, combinations thereof or the like. In some embodiments, strap 52 of wearable electronic device 10 can include latch portions to facilitate latching of wearable electronic device 50. The ornamental design and material construction of strap portion 52 can be adjusted in any manner to suit any designer, manufacturer and/or vendor without departing from the scope of the embodiments described in the present disclosure.

In one or more embodiments, display screen 56 is a screen that can be a liquid crystal display (LCD) screen, transparent LCD screen, light-emitting diode (LED) display screen, transparent LED display screen, organic light-emitting diode (OLED) display screen, transparent LED display screen or any other suitable display screen system. Display screen 56 may also be a touchscreen display, which may include a capacitive or resistive touchscreen layer over the screen of display screen 56.

Wearable electronic device 50 may include ruggedized features, such as a protective housing portion 54 and a protective display screen 56. Skin sensors 58a-58h may also be configured with protective features. Protective housing portion 54, protective display screen 56, and skin sensors 58a-58h may be configured to provide water resistance for electronics (e.g., processors, memory, batteries, display, etc.) for wearable electronic device 50. In one or more embodiments, protective housing portion 54, protective display screen 56, and skin sensors 58a-58h may provide water resistance for up to 200 m. In one or more embodiments, protective housing portion 54, protective display screen 56, and skin sensors 58a-58h may be constructed of materials that may absorb shocks, knocks, falls, or other forms of impacting forces that may be encountered during use of wearable electronic device 50. In one or more embodiments, the materials used to construct protective body protective housing portion 54 and skin sensors 58a-58h may include plastic, rubber, injection molding, neoprene, carbon fiber, polymer, elastomer, silicone, combinations thereof or the like. In one or more embodiments, protective display screen 56 may be constructed of material such as plastic, acrylic, polymers, combinations thereof or the like that may further protect display screen 56 from scratches.

FIG. 5B is a simplified top plan view of wearable electronic device 50 in which display screen 56 is shown disposed on the top surface of housing portion 54 so that it may be visible when wearable electronic device 50 is being worn by the user. FIG. 5C illustrates a simplified bottom view of wearable electronic device 50 in which skin sensors 58a-58h of the sensor array are shown on a bottom surface of strap portion 52 so that it may be in contact with a portion of the skin of the user when wearable electronic device 50 is being worn by the user.

In one or more embodiments, wearable electronic device 50 may further include a wireless communication module configured to communicate the determined general health state of the user with other wireless electronic devices such a wireless communication device associated with the user or an electronic communication device associated with another user. In a particular embodiment, the wireless communication module may be located within housing portion 16. In at least one embodiment, connecting of first clasp portion 14a to second clasp portion 14b may initiate powering up of wearable electronic device 10. In still other embodiments, strap portion 12 may be constructed as a generally ring shaped form with an open portion between ends to facilitate placing of wearable electronic device 10a upon a wrist of a user. In a particular embodiment, logic associated with wearable electronic device 50 may be the same as or similar to that described with respect to FIG. 3 for wearable electronic device 10.

Figure 6:
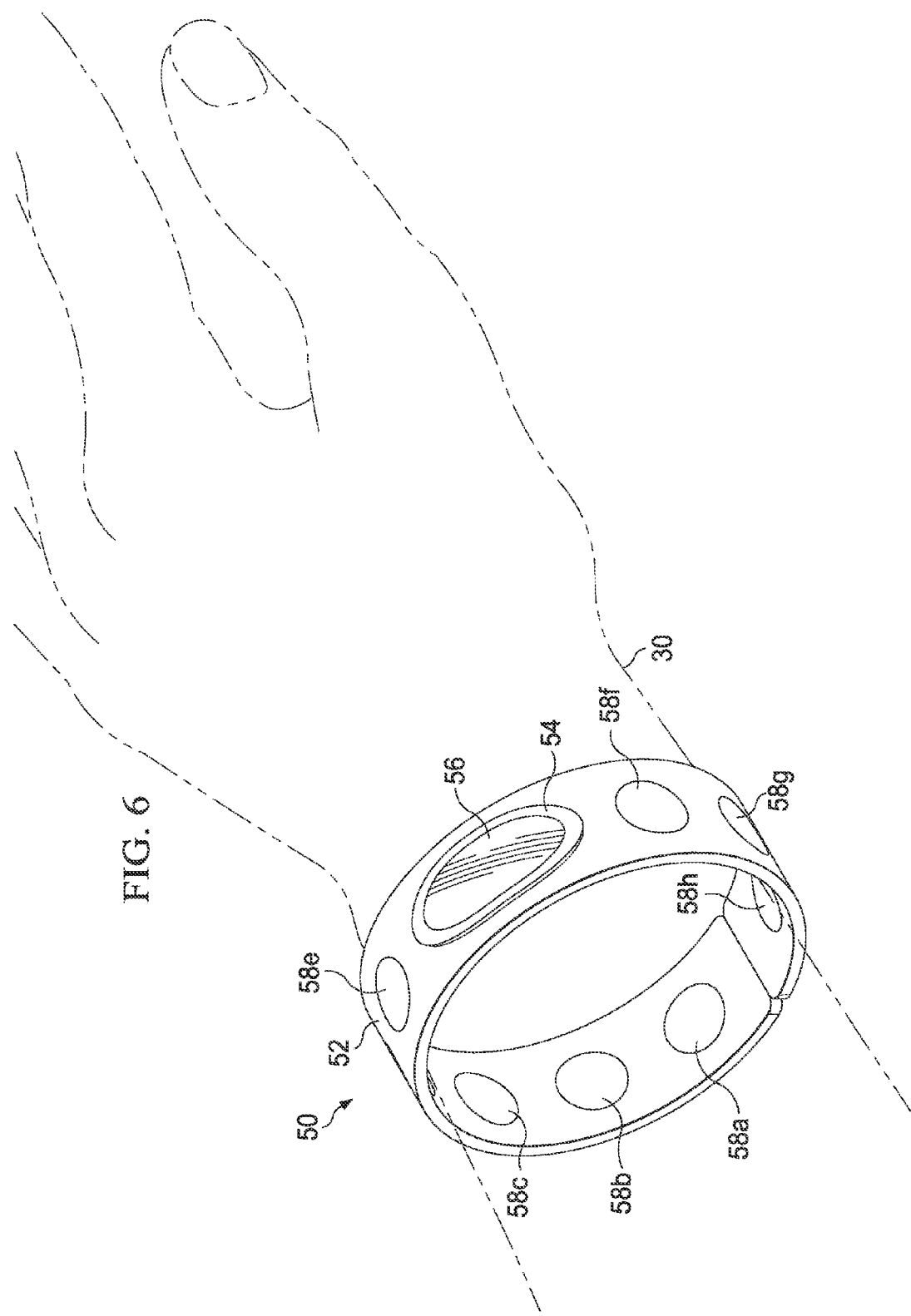
FIG. 6 illustrates an embodiment of an example procedure for determining user health status using the wearable electronic device of FIGS. 5A-5C.

FIG. 6 illustrates an embodiment of an example procedure for determining user health status using wearable electronic device 50 of FIGS. 5A-5C. In the embodiment illustrated in FIG. 6, wearable electronic device 30 is worn upon a wrist 30 of a user. The user may initiate a measurement procedure via a touch input upon a graphical user interface (GUI) provided by display screen 56. In response to the touch input, a control module within housing portion 54 determines one or more sensors 58a-58h of the sensor array to be utilized to measure one or more health parameters, and receives a plurality of health parameter measurements from the determined one or more sensors 58a-58h. For example, health parameters measured by one or more of sensors 58a-58h may include one or more of skin health, bone health, blood health, heart rate, oxygen levels, blood pressure or any other suitable health parameters. In accordance with various embodiments, the sensor array may be used to improve the accuracy of a determined health parameter. For example, the control module may calculate an average value or mean value of the received measurements for a particular health parameter, such as heart rate, to determined an overall value for the particular health parameter.

The control module may be further configured to determine a general health state for the user based upon one or more algorithms using a combination of the received health parameters, and store the general health state in a memory. An example general health state algorithm may include determining whether each health parameters is at an acceptable level. If all of the health parameters are measured to be at an acceptable level, the control module may cause display screen to indicate to the user that the user has achieved an optimal "Prime" health state. Alternately, if the general health state of the user is determined to be poor, the user may be provided with an indication of relative "poor" health. In still other embodiments, the control module may be configured to determine whether a particular health parameter is within an acceptable range and notify the user via display screen 56 if the particular health parameter is not within the acceptable range.

In one or more embodiments, information indicative of the general health state of the user and/or other health or body status information may be sent to another device either in a surrounding area or to a remote device over a network. In a particular embodiment, the information indicative of the general health state of the user may be sent to a second device, such as monitoring device 410, configured to store the information in a database and alert and/or notify a second user of the second device of the general health state of the user of wearable electronic device 50. The second user may include, in some examples, a nurse or doctor at a hospital, or a coach/trainer at an athletic event. In a particular embodiment, wearable electronic device 50 may be used in a communication system the same or similar as communication system 400 discussed with respect to FIG. 4 for wearable electronic device 10.

FIG. 7A is a simplified orthographic view illustrating a monitoring device 410 for receiving user health status from a wearable electronic device in accordance with an embodiment of the present disclosure. Monitoring device 410 can include a strap portion 70 to allow monitoring device 10 to be worn around a wrist of a user. In the embodiment illustrated in FIGURE &A, monitoring device 410 includes a plurality of display screens 72a-72d disposed on an upper surface of a strap portion 70. In accordance with various embodiments, strap portion 70 includes a wireless communication module configured to communicate with one or more of wearable electronic device 10 and/or wearable electronic device 50 to receive a determined general health state and/or other determined health or body parameters or conditions associated with the user of wearable electronic device 10 and/or wearable electronic device 50. Strap portion 70 may further include a control module having components, circuitry, and/or logic configured to notify a user of monitoring device of the received general health state and/or other health/body conditions or parameters via one or more of display screens 72a-72d. Monitoring device 410 may further include a touch input device 74 disposed upon a surface of strap portion 70 configured to allow the user of monitoring device 410 to provide user inputs to wearable electronic device 410.

In one or more embodiments, one or more of strap portion 72a, display screens 72a-72d, and touch input device 74 may be composed of a flexible material to allowing bending to facilitate wearing of monitoring device 410 around the wrist or other body portion of the user. In one or more embodiments, strap portion 70 may be of a solid unibody construction or may include links, chains, cables, weaves, combinations thereof or the like. In some embodiments, strap portion 70 of monitoring device 410 can include latch portions to facilitate latching of monitoring device 410. The ornamental design and material construction of monitoring device 410 can be adjusted in any manner to suit any designer, manufacturer and/or vendor without departing from the scope of the embodiments described in the present disclosure.

In one or more embodiments, one or more of display screens 72a-72d may be a liquid crystal display (LCD) screen, transparent LCD screen, light-emitting diode (LED) display screen, transparent LED display screen, organic light-emitting diode (OLED) display screen, transparent LED display screen or any other suitable display screen system. In some embodiments, one or more of display screens 72a-72d may also be a touchscreen display, which may include a capacitive or resistive touchscreen layer over one or more of the screens of display screens 72a-72d.

FIG. 7B is a simplified top plan view of monitoring device 410 in which display screens 72a-72b and touch input device 74 are shown disposed on the top surface of strap portion 70 so that they may be visible and/or accessible by the user when monitoring device 410 is being worn by the user. FIG. 5C illustrates a simplified bottom view of monitoring device 410.

Figure 8:
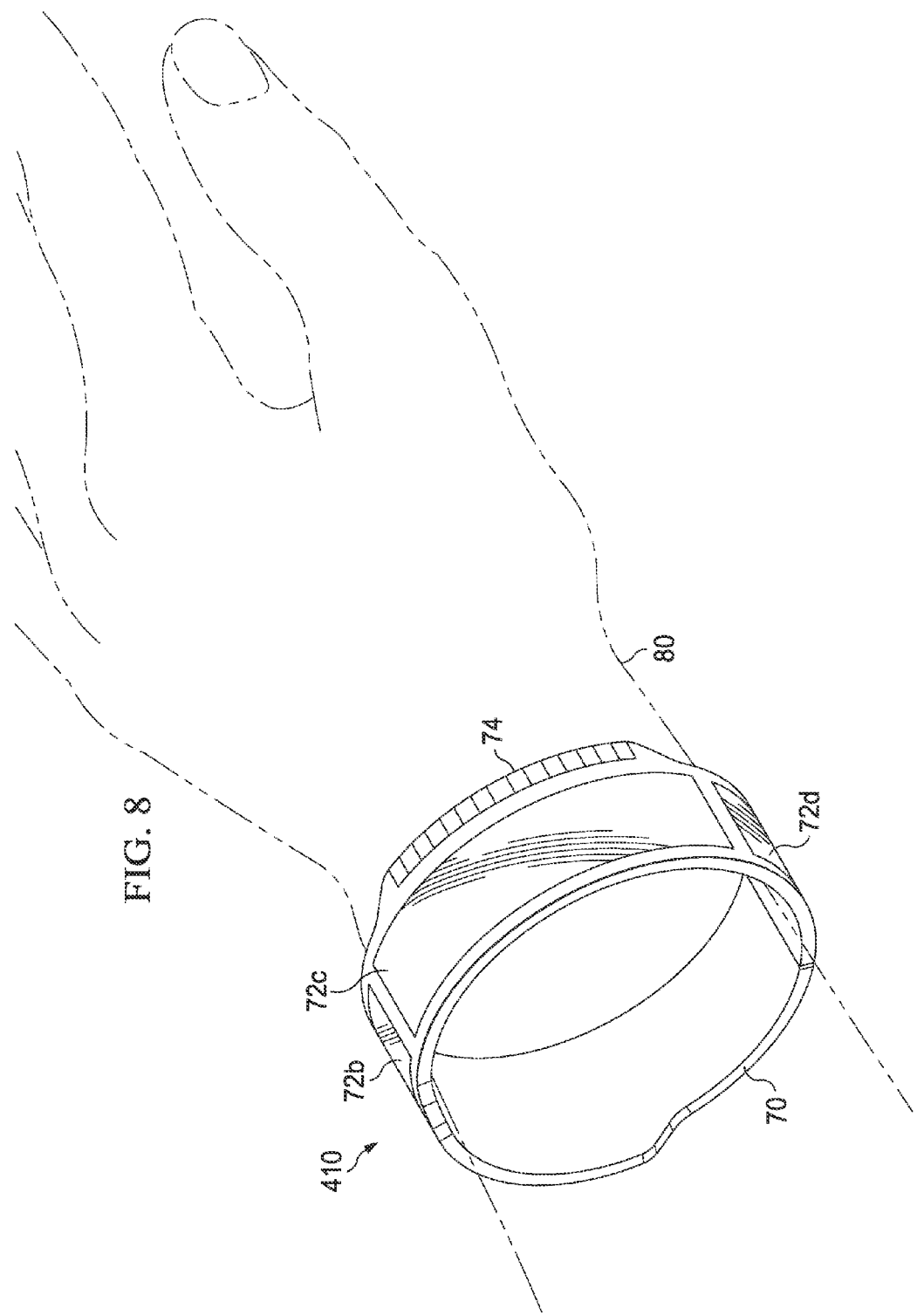
FIG. 8 illustrates an embodiment of an example procedure for receiving user health status from a wearable electronic device using a monitoring device according to one embodiment.

FIG. 8 illustrates an embodiment of an example procedure for receiving user health status from wearable electronic device 10/50 using monitoring device 410 according to one embodiment. In the embodiment illustrated in FIG. 6, monitoring device 410 is worn upon a wrist 80 of a user. In an example operation, wearable electronic device 10 or wearable electronic device 50 sends a first message including information indicative of the health status of the first user associated with wearable electronic device 10/50. In a particular embodiment, wearable electronic device 10/50 may send a message if a particular health parameter or general health status of the first user is determined to be abnormal and/or outside an acceptable range. Upon receiving the first message, monitoring device 410 provides an indication of the general health state of the first user to the second user of monitoring device 410 via one or more of display screens 72a-72d. In a particular embodiment, the indication may include an icon representative of the general health status of the first user displayed in one or more of display screens 72a-72d.

Upon viewing the indication of the general health state of the first user, the second user may interact with touch input device 74 to initiate the sending of a request message by monitoring device 410 to the first user associated with wearable electronic device 10/50 requesting additional information from the first user or requesting the performing of a particular action by the first user. For example, the second user may send a request message including "OK?" or "Please call me." The first user may then use wearable electronic device 10/50 to send a response message to monitoring device 410 including the requested information.

Figure 9:
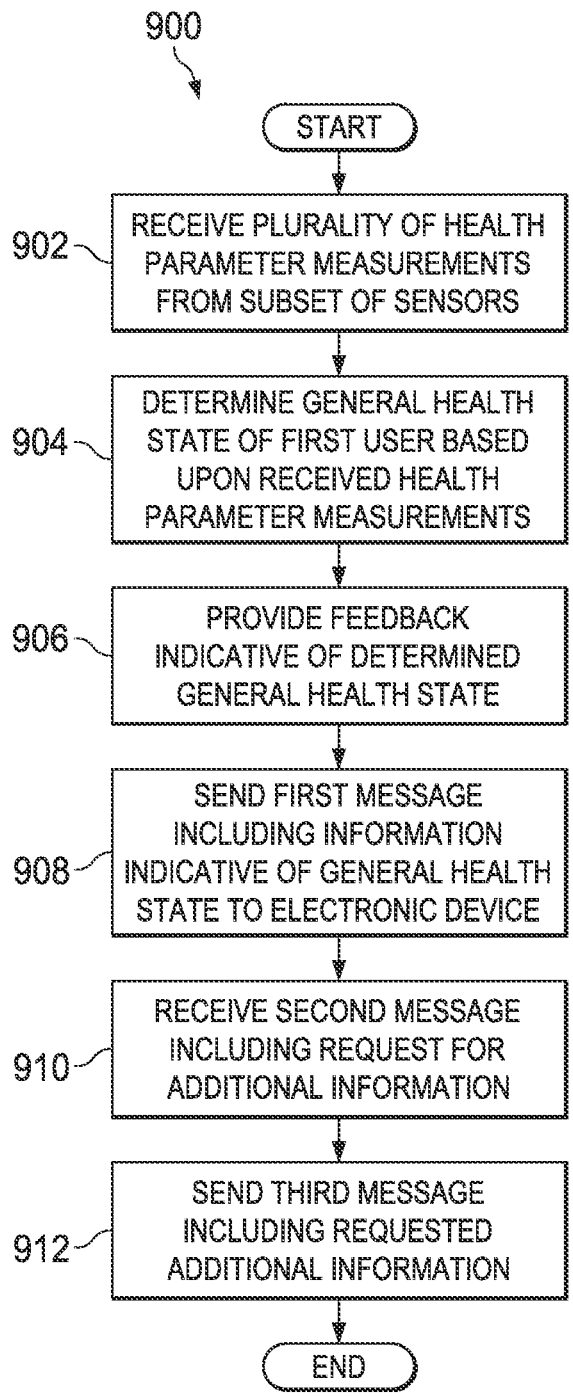
FIG. 9 is a simplified flow diagram illustrating potential operations for a wearable electronic device in accordance with one embodiment of the present disclosure.

Referring now to FIG. 9, FIG. 9 is a simplified flow diagram 900 illustrating potential operations for wearable electronic device 10 in accordance with one embodiment of the present disclosure. In 902, control module 22 of wearable electronic device 10 receives a plurality of health parameter measurements from a subset of the plurality of sensors of sensory array 20 in which each sensor is configured to measure at least one health parameter of a first user associated with the wearable electronic device. In one or more embodiments, the at least one health parameter includes one or more of skin health, bone health, blood health, heart rate, oxygen levels, and blood pressure. In particular embodiments, the subset of the plurality of sensors includes all of the plurality of sensors of sensor array 20.

In 904, control module 22 determines a general health state of the first user based upon the received health parameter measurements. In particular embodiments, control module 22 is configured to determine the general health state of the first user by determining an overall value for one or more particular health parameter measurements, and determining whether the overall value of each health parameter measurement is at an acceptable level.

In 906, display screen 18 provides feedback indicative of the determined general health state to the first user. In a particular embodiment, display screen 18 provides feedback to the first user indicating that the first user has achieved an optimal health state if each of the overall health parameter measurements are determined to be at an acceptable level. In 908, wearable electronic device 10 sends a first message including information indicative of the general health state to an electronic device associated with a second user. In a particular embodiment, the electronic device associated with the second user includes another wearable electronic device such as monitoring device 410.

In 910, wearable electronic device 10 receives a second message from the electronic device associated with the second user that includes a request for additional information from the first user. In 912, wearable electronic device 10 sends a third message to the electronic device associated with the second user in which the third message includes the requested additional information from the first user. The procedure then ends.

The example means and method described above are only a few of the many means and methods that may be used to communicate using wearable communication devices 10 and 50. Virtually any other means could be used, and, thus are clearly within the scope of the present disclosure.

Note that in some example implementations, the functions outlined herein may be implemented in conjunction with logic that is encoded in one or more tangible, non-transitory media (e.g., embedded logic provided in an application-specific integrated circuit (ASIC), in digital signal processor (DSP) instructions, software [potentially inclusive of object code and source code] to be executed by a processor, or other similar machine, etc.). In some of these instances, memory elements can store data used for the operations described herein. This can include the memory elements being able to store software, logic, code, or processor instructions that are executed to carry out the activities described herein. A processor can execute any type of instructions associated with the data to achieve the operations detailed herein. In one example, the processors could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), a DSP, an erasable programmable read only memory (EPROM), electrically erasable programmable read-only memory (EEPROM)) or an ASIC that can include digital logic, software, code, electronic instructions, or any suitable combination thereof.

Program instructions may be used to cause a general-purpose or special-purpose processing system that is programmed with the instructions to perform the operations described herein. Alternatively, the operations may be performed by specific hardware components that contain hardwired logic for performing the operations, or by any combination of programmed computer components and custom hardware components. The methods described herein may be provided as a computer program product that may include one or more non-transitory, tangible, machine readable media having stored thereon instructions that may be used to program a processing system or other electronic device to perform the methods. The term "machine readable medium" used herein shall include any medium that is capable of storing or encoding a sequence of instructions for execution by the machine and that cause the machine to perform any one of the methods described herein. The term "non-transitory machine readable medium" shall accordingly include, but not be limited to, memories* such as solid-state memories, optical and magnetic disks. Furthermore, it is common in the art to speak of software, in one form or another (e.g., program, procedure, process, application, module, logic, and so on) as taking an action or causing a result. Such expressions are merely a shorthand way of stating that the execution of the software by a processing system causes the processor to perform an action or produce a result.

It is imperative to note that all of the specifications, dimensions, and relationships outlined herein (e.g., width, length, thickness, materials, etc.) have only been offered for purposes of example and teaching only. Each of these data may be varied considerably without departing from the spirit of the present disclosure, or the scope of the appended claims. The specifications apply only to one non-limiting example and, accordingly, they should be construed as such. In the foregoing description, example embodiments have been described. Various modifications and changes may be made to such embodiments without departing from the scope of the appended claims. The description and drawings are, accordingly, to be regarded in an illustrative rather than a restrictive sense.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

Example Embodiment Implementations

The following examples pertain to embodiments in accordance with this Specification. Note that all optional features of the apparatuses and systems described above may also be implemented with respect to the method or process described herein and specifics in the examples may be used anywhere in one or more embodiments.

Example 1 is a wearable electronic device, comprising: a plurality of sensors configured to measure at least one health parameter of a first user associated with the wearable electronic device; and a control module in communication with the plurality of sensors, the control module including a processor configured to: receive a plurality of health parameter measurements from at least a subset of the plurality of sensors; and determine a general health state of the first user based upon the received health parameter measurements.

In Example 2, the subject matter of any of Example 1 can optionally include a display configured to provide feedback indicative of the determined general health state to the first user.

In Example 3, the subject matter of any of Examples 1-2 can optionally include wherein the processor is further configured to send a first message including information indicative of the general health state to an electronic device associated with a second user.

In Example 4, the subject matter of any of Examples 1-3 can optionally include wherein the processor is further configured to receive a second message from the electronic device associated with the second user, wherein the second message includes a request for additional information from the first user.

In Example 5, the subject matter of any of Examples 1-4 can optionally include wherein the processor is further configured to send a third message to the electronic device associated with the second user, wherein the third message includes the requested additional information from the first user.

In Example 6, the subject matter of any of Examples 1-3 can optionally include wherein the electronic device associated with the second user includes another wearable electronic device.

In Example 7, the subject matter of any of Examples 1-6 can optionally include wherein the processor is further configured to determine the general health state of the first user by determining an overall value for one or more particular health parameter measurements, and determining whether the overall value of each health parameter measurement is at an acceptable level.

In Example 8, the subject matter of any of Examples 1-7 can optionally include wherein the processor is further configured to provide feedback to the first user indicating that the first user has achieved an optimal health state if each of the overall health parameter measurements are determined to be at an acceptable level.

In Example 9, the subject matter of any of Examples 1-8 can optionally include a strap portion, wherein the plurality of sensors are disposed upon a portion of a surface of the strap portion.

In Example 10, the subject matter of any of Examples 1-9 can optionally include wherein the plurality of health measurements are associated with one or more health parameters of the user, wherein each health parameter is configured to be measured at a plurality of locations upon the surface of the strap portion.

In Example 11, the subject matter of any of Examples 1-10 can optionally include wherein the plurality of sensors comprise a sensor array.

In Example 12, the subject matter of any of Examples 1-11 can optionally include wherein at least one of the plurality of sensors includes at least one of a skin sensor, a temperature sensor, a pulse sensor and a galvanic skin response sensor.

In Example 13, the subject matter of any of Examples 1-12 can optionally include wherein the at least one health parameter includes one or more of body temperature, air temperature, pulse, galvanic skin response, skin health, bone health, blood health, heart rate, oxygen level, and blood pressure.

Example 14 is a wearable electronic device comprising a plurality of sensors configured to measure at least one health parameter of a first user associated with the wearable electronic device, and a control module in communication with the plurality of sensors with the control module including logic, at least a portion of which is partially implemented in hardware, the logic configured to: receive a plurality of health parameter measurements from at least a subset of the plurality of sensors; and determine a general health state of the first user based upon the received health parameter measurements.

In Example 15, the subject matter of Example 14 can optionally include wherein the logic further comprises: at least one processor; and at least one memory.

In Example 16, the subject matter of any of Examples 14-15 can optionally include a display configured to provide feedback indicative of the determined general health state to the first user.

In Example 17, the subject matter of any of Examples 15-16 can optionally include wherein the logic is further configured to send a first message including information indicative of the general health state to an electronic device associated with a second user.

In Example 18, the subject matter of Example 17 can optionally include wherein the logic is further configured to receive a second message from the electronic device associated with the second user, wherein the second message includes a request for additional information from the first user.

In Example 19, the subject matter of Example 18 can optionally include wherein the logic is further configured to send a third message to the electronic device associated with the second user, wherein the third message includes the requested additional information from the first user.

In Example 20, the subject matter of any of Examples 14-19 can optionally include wherein the logic is further configured to determine the general health state of the first user by determining an overall value for one or more particular health parameter measurements, and determining whether the overall value of each health parameter measurement is at an acceptable level.

In Example 21, the subject matter of Example 20 can optionally include wherein the logic is further configured to provide feedback to the first user indicating that the first user has achieved an optimal health state if each of the overall health parameter measurements are determined to be at an acceptable level.

Example 22 is at least one computer readable storage medium comprising instructions, wherein the instructions when executed by at least one processor cause the at least one processor to: receive a plurality of health parameter measurements from at least a subset of a plurality of sensors of a wearable electronic device, wherein each of the plurality of sensors is configured to measure at least one health parameter of a first user associated with the wearable electronic device; and determine, by the wearable electronic device, a general health state of the first user based upon the received health parameter measurements.

In Example 23, the subject matter of Example 22 can optionally include wherein the instructions, when executed by the at least one processor, further cause the at least one processor to provide feedback indicative of the determined general health state to the first user.

In Example 24, the subject matter of any of Examples 22-23 can optionally include wherein the instructions, when executed by the at least one processor, further cause the at least one processor to send a first message including information indicative of the general health state to an electronic device associated with a second user.

In Example 25, the subject matter of Example 24 can optionally include wherein the instructions, when executed by the at least one processor, further cause the at least one processor to receive a second message from the electronic device associated with the second user, wherein the second message includes a request for additional information from the first user.

In Example 26, the subject matter of any of Examples 22-25 can optionally include wherein the instructions, when executed by the at least one processor, further cause the at least one processor to determine the general health state of the first user by determining an overall value for one or more particular health parameter measurements, and determining whether the overall value of each health parameter measurement is at an acceptable level.

In Example 27, the subject matter of Example 26 can optionally include wherein the instructions, when executed by the at least one processor, further cause the at least one processor to provide feedback to the first user indicating that the first user has achieved an optimal health state if each of the overall health parameter measurements are determined to be at an acceptable level.

Example 28 is a method comprising: receiving a plurality of health parameter measurements from at least a subset of a plurality of sensors of a wearable electronic device, wherein each of the plurality of sensors is configured to measure at least one health parameter of a first user associated with the wearable electronic device; and determining, by the wearable electronic device, a general health state of the first user based upon the received health parameter measurements.

In Example 29, the subject matter of Example 28 can optionally include providing feedback indicative of the determined general health state to the first user.

In Example 30, the subject matter of any of Examples 28-29 can optionally include sending a first message including information indicative of the general health state to an electronic device associated with a second user.

In Example 31, the subject matter of Example 30 can optionally include receiving a second message from the electronic device associated with the second user, wherein the second message includes a request for additional information from the first user.

In Example 32, the subject matter of any of Examples 28-31 can optionally include determining the general health state of the first user by determining an overall value for one or more particular health parameter measurements, and determining whether the overall value of each health parameter measurement is at an acceptable level.

In Example 33, the subject matter of Example 32 can optionally include providing feedback to the first user indicating that the first user has achieved an optimal health state if each of the overall health parameter measurements are determined to be at an acceptable level.

Example 34 is an apparatus comprising means for performing the method of any one of Examples 28-33.

In Example 35, the subject matter of Example 34 can optionally include wherein the means for performing the method comprise a processor and a memory.

In Example 36, the subject of Example 35 can optionally include wherein the memory comprises machine readable instructions, that when executed cause the apparatus to perform the method of any one of Examples 28-33.

In Example 37, the subject matter of any of Examples 34-36 can optionally include wherein the apparatus is a computing system.

Example 38 is at least one computer readable medium comprising instructions that, when executed, implement a method or realize an apparatus as described in any one of Examples 1-21 or 28-37.

Example 39 is an apparatus comprising: means for receiving a plurality of health parameter measurements from at least a subset of a plurality of sensors of a wearable electronic device, wherein each of the plurality of sensors is configured to measure at least one health parameter of a first user associated with the wearable electronic device; and determining, by the wearable electronic device, a general health state of the first user based upon the received health parameter measurements.

In Example 40, the subject matter of Example 39 can optionally include means for providing feedback indicative of the determined general health state to the first user.

In Example 41, the subject matter of any of Examples 39-40 can optionally include means for sending a first message including information indicative of the general health state to an electronic device associated with a second user.

In Example 42, the subject matter of any of Examples 39-41 can optionally include means for receiving a second message from the electronic device associated with the second user, wherein the second message includes a request for additional information from the first user.

In Example 43, the subject matter of any of Examples 39-42 can optionally include means for determining the general health state of the first user by determining an overall value for one or more particular health parameter measurements, and determining whether the overall value of each health parameter measurement is at an acceptable level.

In Example 44, the subject matter of Example 43 can optionally include means for providing feedback to the first user indicating that the first user has achieved an optimal health state if each of the overall health parameter measurements are determined to be at an acceptable level.

What is claimed is:

1. A wearable electronic device, comprising:
   a plurality of sensors configured to measure at least one health parameter of a first user associated with the wearable electronic device;
   a control module in communication with the plurality of sensors, the control module including a processor configured to:
      receive a plurality of different health parameter measurements from at least a subset of the plurality of sensors;

determine an overall value for each of a plurality of particular health parameters by calculating a mean value of each received different health parameter measurement for the particular health parameter;
determine a general health state of the first user based upon a combination of the determined overall values of each of the plurality of particular health parameters;
send a first message including information indicative of the general health state to an electronic device associated with a second user, wherein the electronic device associated with the second user includes another wearable electronic device; and
receive a second message from the electronic device associated with the second user, wherein the second message includes a request for additional information from the first user; and
a display configured to provide feedback indicative of the determined general health state to the first user and the second received message.

2. The wearable electronic device of claim 1, wherein the processor is further configured to send a third message to the electronic device associated with the second user, wherein the third message includes the requested additional information from the first user.

3. The wearable electronic device of claim 1, wherein the processor is further configured to determine the general health state of the first user by determining whether the overall value of each health parameter measurement is at an acceptable level.

4. The wearable electronic device of claim 3, wherein the processor is further configured to provide feedback to the first user indicating that the first user has achieved an optimal health state if each of the overall health parameter measurements are determined to be at an acceptable level.

5. The wearable electronic device of claim 1, further comprising a strap portion, wherein the plurality of sensors are disposed upon a portion of a surface of the strap portion.

6. The wearable electronic device of claim 5, wherein the plurality of health measurements are associated with one or more health parameters of the user, wherein each health parameter is configured to be measured at a plurality of locations upon the surface of the strap portion.

7. The wearable electronic device of claim 1, wherein the plurality of sensors comprise a sensor array.

8. The wearable electronic device of claim 1, wherein at least one of the plurality of sensors includes at least one of a skin sensor, a temperature sensor, a pulse sensor and a galvanic skin response sensor.

9. The wearable electronic device of claim 1, wherein the at least one health parameter includes one or more of body temperature, air temperature, pulse, galvanic skin response, skin health, bone health, blood health, heart rate, oxygen level, and blood pressure.

10. A wearable electronic device comprising a plurality of sensors configured to measure at least one health parameter of a first user associated with the wearable electronic device, and a control module in communication with the plurality of sensors with the control module including logic, at least a portion of which is partially implemented in hardware, the logic configured to:
receive a plurality of different health parameter measurements from at least a subset of the plurality of sensors;
determine an overall value for each of a plurality of particular health parameters by calculating a mean value of each received different health parameter measurement for the particular health parameter;
determine a general health state of the first user based upon a combination of the determined overall values of each of the plurality of particular health parameters;
send a first message including information indicative of the general health state to an electronic device associated with a second user, wherein the electronic device associated with the second user includes another wearable electronic device;
receive a second message from the electronic device associated with the second user, wherein the second message includes a request for additional information from the first user; and
provide feedback indicative of the determined general health state to the first user and the received second message.

11. The wearable electronic device of claim 10, wherein the logic further comprises:
at least one processor; and
at least one memory.

12. The wearable electronic device of claim 10, further comprising a display configured to provide the feedback indicative of the determined general health state to the first user.

13. The wearable electronic device of claim 10, wherein the logic is further configured to send a third message to the electronic device associated with the second user, wherein the third message includes the requested additional information from the first user.

14. The wearable electronic device of claim 10, wherein the logic is further configured to determine the general health state of the first user by determining whether the overall value of each health parameter measurement is at an acceptable level.

15. The wearable electronic device of claim 14, wherein the logic is further configured to provide feedback to the first user indicating that the first user has achieved an optimal health state if each of the overall health parameter measurements are determined to be at an acceptable level.

16. At least one non-transitory computer readable storage medium comprising instructions, wherein the instructions when executed by at least one processor cause the at least one processor to:
receive a plurality of different health parameter measurements from at least a subset of a plurality of sensors of a wearable electronic device, wherein each of the plurality of sensors is configured to measure at least one health parameter of a first user associated with the wearable electronic device; and
determine an overall value for each of a plurality of particular health parameters by calculating a mean value of each received different health parameter measurement for the particular health parameter;
determine a general health state of the first user based upon a combination of the determined overall values of each of the plurality of particular health parameters;
send a first message including information indicative of the general health state to an electronic device associated with a second user, wherein the electronic device associated with the second user includes another wearable electronic device;
receive a second message from the electronic device associated with the second user, wherein the second message includes a request for additional information from the first user; and provide feedback indicative of the determined general health state to the first user and the received second message.

\* \* \* \* \*